US011382652B2

(12) United States Patent
Wasdyke et al.

(10) Patent No.: US 11,382,652 B2
(45) Date of Patent: Jul. 12, 2022

(54) DEVICE GUIDEWIRE MANAGEMENT ACCESSORY

(71) Applicant: BOSTON SCIENTIFIC SCIMED, INC., Maple Grove, MN (US)

(72) Inventors: Joel M. Wasdyke, Eden Prairie, MN (US); Jason T. Anderson, Deephaven, MN (US); Patrick A. Haverkost, Corcoran, MN (US); Joel N. Groff, Delano, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 173 days.

(21) Appl. No.: 16/405,979

(22) Filed: May 7, 2019

(65) Prior Publication Data
US 2019/0343551 A1 Nov. 14, 2019

Related U.S. Application Data

(60) Provisional application No. 62/668,625, filed on May 8, 2018.

(51) Int. Cl.
*A61B 17/3207* (2006.01)
*A61M 25/09* (2006.01)
*A61B 17/32* (2006.01)

(52) U.S. Cl.
CPC ........... *A61B 17/320758* (2013.01); *A61M 25/09041* (2013.01); *A61B 17/32002* (2013.01); *A61M 2025/09125* (2013.01)

(58) Field of Classification Search
CPC ...... A61B 17/320758; A61B 17/32002; A61B 17/3207; A61B 2017/22038; A61M 25/09041; A61M 2025/09125
See application file for complete search history.

(56) References Cited

U.S. PATENT DOCUMENTS 5,314,407 A    5/1994   Auth et al.
5,855,567 A    1/1999   Reesemann
(Continued)

FOREIGN PATENT DOCUMENTS

WO    20008042987 A2    4/2008

OTHER PUBLICATIONS

Boston Scientific, "Jetstream System Brochure", pp. 1-6, Oct. 2015. https:www.bostonscientific.com/content/dam/bostonscientific/pi/porffolio-group/Atherectomy/Jetstream%20System%20Brochure%20PI-273812-AB%20OCT2015.pdf.
(Continued)

*Primary Examiner* — Kathleen S Holwerda
*Assistant Examiner* — Lauren Dubose
(74) *Attorney, Agent, or Firm* — Seager, Tufte & Wickhem, LLP

(57) ABSTRACT

An atherectomy system may include an atherectomy apparatus including a drive housing, a catheter shaft extending distally from the drive housing, and a rotatable drive shaft extending within the catheter shaft and operably coupled to the drive housing, the rotatable drive shaft having a guidewire lumen configured to receive a guidewire; and a guidewire management device including: a frame including at least one frame rail extending longitudinally; a movable tray slidably coupled to the at least one frame rail; and a guidewire locking element fixed to the frame. The drive housing may be releasably secured to the movable tray.

20 Claims, 5 Drawing Sheets

(56) References Cited

U.S. PATENT DOCUMENTS

| | | | |
|---|---|---|---|
| 6,149,663 | A | 11/2000 | Strandberg et al. |
| 6,565,588 | B1 | 5/2003 | Clement et al. |
| 6,599,265 | B2 | 7/2003 | Bon |
| 6,818,001 | B2 | 11/2004 | Wulfman et al. |
| 7,344,546 | B2 | 3/2008 | Wulfman et al. |
| 7,390,323 | B2 | 6/2008 | Jang |
| 7,632,241 | B2 | 12/2009 | Raijman et al. |
| 7,674,272 | B2 | 3/2010 | Torrance et al. |
| 7,713,231 | B2 | 5/2010 | Wulfman et al. |
| 7,713,235 | B2 | 5/2010 | Torrance et al. |
| 8,092,397 | B2 | 1/2012 | Wallace et al. |
| 8,323,240 | B2 | 12/2012 | Wulfman et al. |
| 8,435,228 | B2 | 5/2013 | Wulfman et al. |
| 8,523,824 | B2 | 9/2013 | Teirstein et al. |
| 9,108,027 | B2 | 8/2015 | Eubanks et al. |
| 2002/0007190 | A1* | 1/2002 | Wulfman ....... A61B 17/320758 606/167 |
| 2004/0235611 | A1 | 11/2004 | Nistal |
| 2004/0243162 | A1 | 12/2004 | Wulfman et al. |
| 2006/0041245 | A1 | 2/2006 | Ferry et al. |
| 2007/0282167 | A1 | 12/2007 | Barenboym et al. |
| 2009/0287188 | A1 | 11/2009 | Golden et al. |
| 2011/0040238 | A1 | 2/2011 | Wulfman et al. |
| 2011/0105954 | A1 | 5/2011 | Cohen et al. |
| 2013/0035537 | A1* | 2/2013 | Wallace ................. A61B 34/30 600/8 |
| 2013/0237763 | A1 | 9/2013 | Qiu |
| 2014/0243734 | A1* | 8/2014 | Eubanks ......... A61M 25/09041 604/22 |
| 2017/0189056 | A1 | 7/2017 | Nakano |

OTHER PUBLICATIONS

International Search Report and Written Opinion dated May 16, 2014 for International Application No. PCT/US2014/017842.
International Search Report and Written Opinion dated Jul. 18, 2019 for International Application No. PCT/US2019/031220.

* cited by examiner

DEVICE GUIDEWIRE MANAGEMENT ACCESSORY

CROSS-REFERENCE TO RELATED APPLICATIONS

This application claims the benefit of priority under 35 U.S.C. § 119 of U.S. Provisional Application No. 62/668,625, filed May 8, 2018, the entire disclosure of which is hereby incorporated by reference.

TECHNICAL FIELD

The present disclosure pertains to medical devices and methods for using medical devices. More particularly, the present disclosure pertains to aspects of medical devices and/or means to manage a guidewire used with medical devices.

BACKGROUND

A wide variety of intracorporeal medical devices have been developed for medical use, for example, surgical and/or intravascular use. Some of these devices include guidewires, catheter systems, medical device delivery systems (e.g., for stents, grafts, replacement valves, occlusive medical devices, etc.), atherectomy systems, and the like. These devices are manufactured by any one of a variety of different manufacturing methods and may be used according to any one of a variety of methods. There is an ongoing need to provide alternative medical devices as well as alternative methods for manufacturing and/or using medical devices.

SUMMARY

In a first aspect, an atherectomy system may comprise an atherectomy apparatus including a drive housing, a catheter shaft extending distally from the drive housing, and a rotatable drive shaft extending within the catheter shaft and operably coupled to the drive housing, the rotatable drive shaft having a guidewire lumen configured to receive a guidewire; and a guidewire management device comprising: a frame including at least one frame rail extending longitudinally; a movable tray slidably coupled to the at least one frame rail; and a guidewire locking element fixed to the frame. The drive housing may be releasably secured to the movable tray.

In addition or alternatively, and in a second aspect, the guidewire locking element is configured to slidably receive the guidewire.

In addition or alternatively, and in a third aspect, the guidewire locking element is configured to selectively secure the guidewire in place relative to the frame.

In addition or alternatively, and in a fourth aspect, selectively securing the guidewire in place relative to the frame prevents both longitudinal and rotational movement of the guidewire relative to the frame.

In addition or alternatively, and in a fifth aspect, the catheter shaft is removably secured to the drive housing.

In addition or alternatively, and in a sixth aspect, the catheter shaft is fixed in position relative to the drive housing.

In addition or alternatively, and in a seventh aspect, the rotatable drive shaft is rotatable relative to the guidewire.

In addition or alternatively, and in an eighth aspect, the drive housing includes a motor disposed within the drive housing, the motor being configured to rotate the rotatable drive shaft relative to the catheter shaft.

In addition or alternatively, and in a ninth aspect, the drive housing includes a longitudinal lumen in communication with the guidewire lumen of the drive shaft, the longitudinal lumen being configured to receive the guidewire such that the drive housing is slidable over the guidewire.

In addition or alternatively, and in a tenth aspect, an atherectomy system may comprise an atherectomy apparatus including a drive housing, a catheter shaft extending from a distal end of the drive housing, and a rotatable drive shaft extending within the catheter shaft and operably coupled to a motor within the drive housing, the rotatable drive shaft having a guidewire lumen configured to receive a guidewire; and a guidewire management device comprising: a frame including at least one frame rail extending longitudinally; a movable tray slidably coupled to the at least one frame rail; and a guidewire locking element fixed to the frame. The catheter shaft may be removably secured to the drive housing and non-rotatable relative to the drive housing when secured to the drive housing. The guidewire locking element may be configured to longitudinally secure the guidewire relative to the frame. The rotatable drive shaft may be configured to rotate relative to the guidewire and the catheter shaft. The drive housing may be configured to slide along the guidewire.

In addition or alternatively, and in an eleventh aspect, the atherectomy apparatus includes a rotatable cutting head fixed to a distal end of the rotatable drive shaft.

In addition or alternatively, and in a twelfth aspect, the guidewire locking element is configured to prevent relative rotational movement between the guidewire and the frame.

In addition or alternatively, and in a thirteenth aspect, the drive housing is configured to be releasably secured to the movable tray.

In addition or alternatively, and in a fourteenth aspect, the at least one frame rail includes two frame rails extending longitudinally along a base of the frame.

In addition or alternatively, and in a fifteenth aspect, a guidewire management device may comprise a frame including a base, a proximal upright, a distal upright, and at least one frame rail extending from the proximal upright to the distal upright; a movable tray slidably coupled to the at least one frame rail; and a guidewire locking element secured to the proximal upright.

In addition or alternatively, and in a sixteenth aspect, the at least one frame rail is oriented substantially parallel to the base.

In addition or alternatively, and in a seventeenth aspect, the guidewire locking element includes an aperture passing through the proximal upright generally parallel to the base.

In addition or alternatively, and in an eighteenth aspect, the proximal upright and the distal upright extend from a proximal end and a distal end of the base, respectively, at an oblique angle to the base.

In addition or alternatively, and in a nineteenth aspect, a free end of the proximal upright extends a greater distance from the base than a free end of the distal upright.

In addition or alternatively, and in a twentieth aspect, the proximal upright and the distal upright are integrally formed with the base.

The above summary of some embodiments, aspects, and/or examples is not intended to describe each embodiment or every implementation of the present disclosure. The figures and the detailed description which follows more particularly exemplify these embodiments.

BRIEF DESCRIPTION OF THE DRAWINGS

The disclosure may be more completely understood in consideration of the following detailed description of various embodiments in connection with the accompanying drawings, in which.

Figure 1:
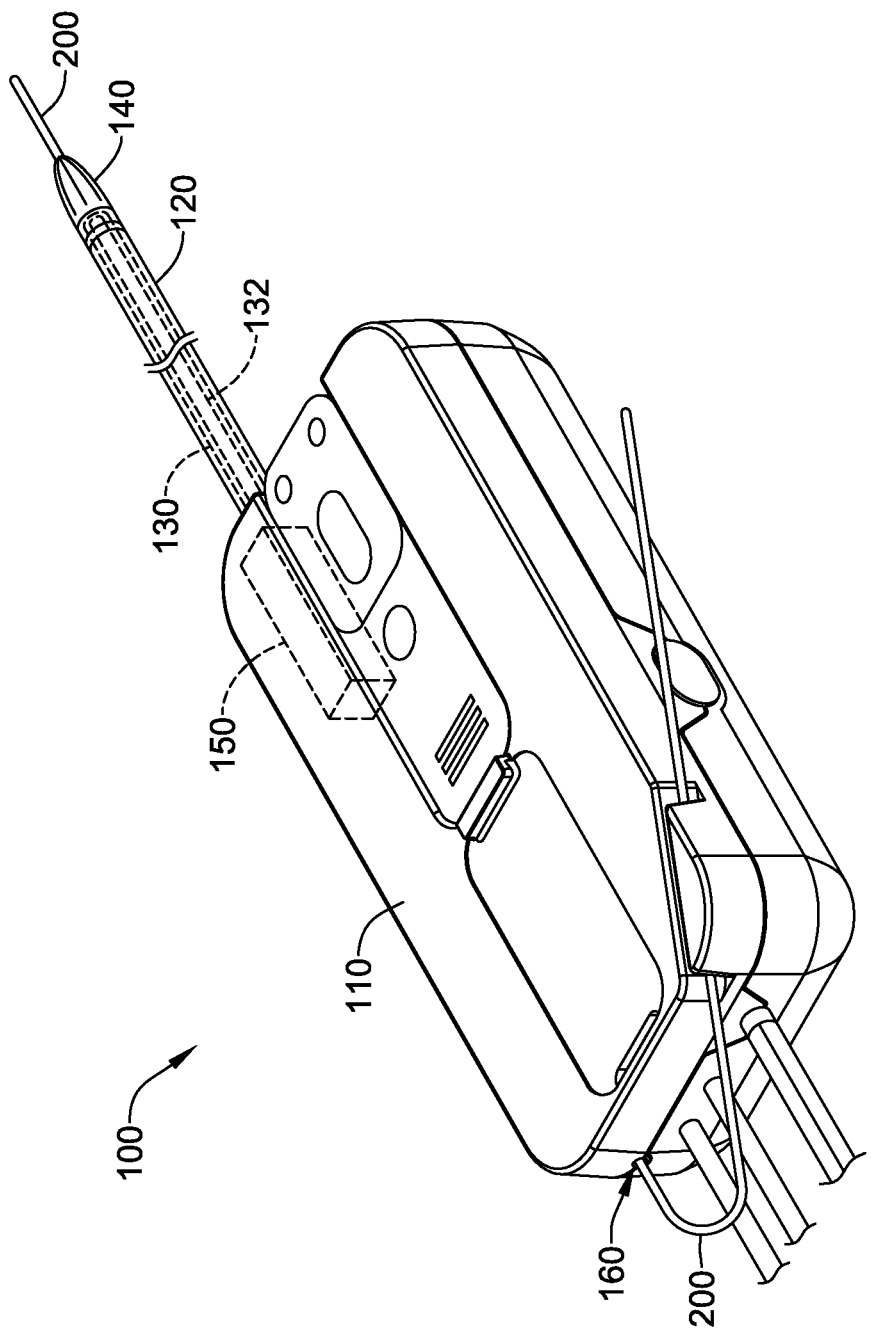
FIG. 1 illustrates aspects of an example atherectomy apparatus.

While aspects of the disclosure are amenable to various modifications and alternative forms, specifics thereof have been shown by way of example in the drawings and will be described in detail. It should be understood, however, that the intention is not to limit aspects of the disclosure to the particular embodiments described. On the contrary, the intention is to cover all modifications, equivalents, and alternatives falling within the spirit and scope of the disclosure.

DETAILED DESCRIPTION

The following description should be read with reference to the drawings, which are not necessarily to scale, wherein like reference numerals indicate like elements throughout the several views. The detailed description and drawings are intended to illustrate but not limit the claimed invention. Those skilled in the art will recognize that the various elements described and/or shown may be arranged in various combinations and configurations without departing from the scope of the disclosure. The detailed description and drawings illustrate example embodiments of the claimed invention. However, in the interest of clarity and ease of understanding, while every feature and/or element may not be shown in each drawing, the feature(s) and/or element(s) may be understood to be present regardless, unless otherwise specified.

For the following defined terms, these definitions shall be applied, unless a different definition is given in the claims or elsewhere in this specification.

All numeric values are herein assumed to be modified by the term "about," whether or not explicitly indicated. The term "about", in the context of numeric values, generally refers to a range of numbers that one of skill in the art would consider equivalent to the recited value (e.g., having the same function or result). In many instances, the term "about" may include numbers that are rounded to the nearest significant figure. Other uses of the term "about" (e.g., in a context other than numeric values) may be assumed to have their ordinary and customary definition(s), as understood from and consistent with the context of the specification, unless otherwise specified.

The recitation of numerical ranges by endpoints includes all numbers within that range, including the endpoints (e.g., 1 to 5 includes 1, 1.5, 2, 2.75, 3, 3.80, 4, and 5).

Although some suitable dimensions, ranges, and/or values pertaining to various components, features and/or specifications are disclosed, one of skill in the art, incited by the present disclosure, would understand desired dimensions, ranges, and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise. It is to be noted that in order to facilitate understanding, certain features of the disclosure may be described in the singular, even though those features may be plural or recurring within the disclosed embodiment(s). Each instance of the features may include and/or be encompassed by the singular disclosure(s), unless expressly stated to the contrary. For simplicity and clarity purposes, not all elements of the disclosed invention are necessarily shown in each figure or discussed in detail below. However, it will be understood that the following discussion may apply equally to any and/or all of the components for which there are more than one, unless explicitly stated to the contrary. Additionally, not all instances of some elements or features may be shown in each figure for clarity.

Relative terms such as "proximal", "distal", "advance", "retract", variants thereof, and the like, may be generally considered with respect to the positioning, direction, and/or operation of various elements relative to a user/operator/manipulator of the device, wherein "proximal" and "retract" indicate or refer to closer to or toward the user and "distal" and "advance" indicate or refer to farther from or away from the user. In some instances, the terms "proximal" and "distal" may be arbitrarily assigned in an effort to facilitate understanding of the disclosure, and such instances will be readily apparent to the skilled artisan. Other relative terms, such as "upstream", "downstream", "inflow", and "outflow" refer to a direction of fluid flow within a lumen, such as a body lumen, a blood vessel, or within a device. Still other relative terms, such as "axial", "circumferential", "longitudinal", "lateral", "radial", etc. and/or variants thereof generally refer to direction and/or orientation relative to a central longitudinal axis of the disclosed structure or device.

The terms "extent" and/or "maximum extent" may be understood to mean a greatest measurement of a stated or identified dimension, while the term "minimum extent" may be understood to mean a smallest measurement of a stated or identified dimension. For example, "outer extent" may be understood to mean a maximum outer dimension, "radial extent" may be understood to mean a maximum radial dimension, "longitudinal extent" may be understood to mean a maximum longitudinal dimension, etc. Each instance of an "extent" may be different (e.g., axial, longitudinal, lateral, radial, circumferential, etc.) and will be apparent to the skilled person from the context of the individual usage. Generally, an "extent" or "maximum extent" may be considered a greatest possible dimension measured according to the intended usage. Alternatively, a "minimum extent" may be considered a smallest possible dimension measured according to the intended usage. In some instances, an "extent" may generally be measured orthogonally within a plane and/or cross-section, but may be, as will be apparent from the particular context, measured differently—such as, but not limited to, angularly, radially, circumferentially (e.g., along an arc), etc.

It is noted that references in the specification to "an embodiment", "some embodiments", "other embodiments", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it would be within the knowledge of one skilled in the art to effect the particular feature, structure, or characteristic in connection with other embodiments, whether or not explicitly described, unless clearly stated to the contrary. That is, the various individual elements described below, even if not explicitly shown in a particular combination, are nevertheless contemplated as being combinable or arrangeable with each other to form other additional embodiments or to complement and/or enrich the described embodiment(s), as would be understood by one of ordinary skill in the art.

For the purpose of clarity, certain identifying numerical nomenclature (e.g., first, second, third, fourth, etc.) may be used throughout the description and/or claims to name and/or differentiate between various described and/or claimed features. It is to be understood that the numerical nomenclature is not intended to be limiting and is exemplary only. In some embodiments, alterations of and deviations from previously-used numerical nomenclature may be made in the interest of brevity and clarity. That is, a feature identified as a "first" element may later be referred to as a "second" element, a "third" element, etc. or may be omitted entirely, and/or a different feature may be referred to as the "first" element. The meaning and/or designation in each instance will be apparent to the skilled practitioner.

Diseases and/or medical conditions that impact the cardiovascular system are prevalent throughout the world. Interventional techniques for removing disease such as atherosclerotic plaque, thrombus, and other types of material forming obstructions and partial obstructions from internal body lumens or cavities using interventional catheters are well-established. Interventional catheters may employ operating heads that break down and/or remove occlusive material using mechanical structures such as cutter assemblies, abrasive materials and/or shaped tools, excision devices, ablation instruments employing modalities such as RF, laser or radiation-induced ablation modalities, ultrasound, fluid jets or fluid agitation, and the like. Other types of interventional catheters may provide fluid infusion and/or aspiration alone, or in combination with another diagnostic or treatment modality. Many of these systems involve placement of a guiding catheter and/or guidewire prior to introduction of the interventional catheter, facilitating navigation of the interventional catheter to the target intervention site and manipulation of the interventional catheter at the target intervention site over the guidewire.

Many material removal devices and interventional catheters incorporate mechanical aspiration systems to remove the ablated material from the site and some systems incorporate or are used in conjunction with other mechanisms such as distal filters for preventing removed material from circulating in the blood stream. Some interventional catheter systems incorporate or are used in conjunction with a fluid infusion system providing delivery of fluids to an interventional site. Interventional catheter systems may also incorporate or be used in conjunction with imaging systems and other types of complementary and/or auxiliary tools and features that facilitate desirable placement and operation of the system during an interventional procedure.

Interventional catheters are generally mounted to controller housing drive mechanisms, fluid manifolds and management systems, and the like, at a proximal end of the catheter. Some types of interventional catheters employ a single operational and control component interfacing with and mounted to the interventional catheter. In devices that interface with a single operating and control component, system operating components may be housed in the control component and user interface controls for operating the catheter and operating head are provided on the operating and control component. Various control features for activating and operating the interventional catheter, its aspiration and/or infusion systems, and/or its operating head may be provided. Status indicators, system read-outs, and operating information may also be provided on interventional catheter operating and control components.

Many interventional catheter systems are used in combination with a guidewire, which is navigated to a target intervention site and then aids safe navigation of the interventional catheter, over the guidewire, to the target intervention site. The guidewire also facilitates positioning and movement of the interventional catheter over the guidewire at the target intervention site during the interventional procedure. When interventional catheter systems are employed as atherectomy or thrombectomy devices, for example, a guidewire is generally introduced into a patient's vasculature and advanced until its distal end is positioned at a location distal to an occlusion and/or the target intervention site. The interventional catheter is then advanced over the guidewire to a location just proximal to the occlusion and/or the target intervention site. During an intervention, the distal end of the interventional catheter is generally advanced and retracted over the guidewire through the occlusion and/or the target intervention site in distal and proximal directions, respectively, at least once and sometimes repeatedly, to remove occlusive tissue. Many other types of interventional catheter systems also involve translation of an interventional catheter over a guidewire prior to and/or during an intervention.

The guidewire generally traverses an internal guidewire lumen in the interventional catheter assembly and is generally routed into and through a controller or housing provided at the proximal end of the interventional catheter, exiting the controller at another location. Occasionally, when attempting to move the interventional catheter and/or the controller relative to the guidewire, the guidewire may move along with the interventional catheter and/or the controller due to its length, binding between the devices through tortuous anatomy, etc. Uncontrolled movement of the guidewire may present certain risks to the patient.

There remains a need for improved performance of interventional catheter assemblies over guidewires, as well as for improved devices and methods for manipulating, adjusting, limiting or otherwise managing the relative movement and/or positioning of guidewires relative to interventional catheters and/or controllers during an intervention. Improved management of guidewire positioning relative to an interventional catheter assembly and/or controller may result in faster, safer, and more effective catheter-based interventional treatments. The apparatus, devices, and methods disclosed herein may also provide a number of additional desirable features and/or benefits as described herein.

FIG. 1 illustrates an example atherectomy apparatus 100 including a drive housing 110, a catheter shaft 120 extending distally from the drive housing 110, and a rotatable drive shaft 130 (shown in phantom) extending within the catheter shaft 120 and operably coupled to the drive housing 110. The rotatable drive shaft 130 may have and/or include a guidewire lumen 132 extending through and/or within the rotatable drive shaft 130. In some embodiments, the guidewire lumen 132 of the rotatable drive shaft 130 may extend from a proximal end of the rotatable drive shaft 130 to a distal end of the rotatable drive shaft 130. In at least some embodiments, the guidewire lumen 132 of the rotatable drive shaft 130 may be configured to slidably and/or rotatably receive a guidewire 200. In FIG. 1, the drive housing 110 is schematically illustrated as being mounted on or over the guidewire 200.

In some embodiments, the catheter shaft 120 may be removably secured to a distal portion and/or a distal end of the drive housing 110. For example, the catheter shaft 120 may be removable from the drive housing 110 for replacement, cleaning, sterilization, etc. In some embodiments, when the catheter shaft 120 is removably secured to the drive housing 110, the catheter shaft 120 may be fixed in position relative to the drive housing 110. For example, the catheter shaft 120 may be non-rotatable relative to the drive housing 110 when secured to the drive housing 110. In some embodiments, the rotatable drive shaft 130 and the catheter shaft 120 may be coupled together as a replaceable catheter assembly. In at least some embodiments, the rotatable drive shaft 130 may be rotatable and/or may be configured to rotate relative to the catheter shaft 120 and/or the guidewire 200.

The atherectomy apparatus 100 may include a rotatable cutting head 140 fixed to a distal end of the rotatable drive shaft 130. In some embodiments, the rotatable cutting head 140 may be removable from the distal end of the rotatable drive shaft 130. The rotatable cutting head 140 may include a blade-type cutting head, a burr-type cutting head, a grinding-type cutting head, a macerator, or other suitable cutting head. The rotatable cutting head 140 may be rotatable relative to the catheter shaft 120 and/or the guidewire 200. Rotation of the rotatable drive shaft 130 may cause and/or result in corresponding rotation of the rotatable cutting head 140.

In some embodiments, the drive housing 110 may include a motor 150 (shown in phantom) disposed within the drive housing 110. The motor 150 may be configured to rotate the rotatable drive shaft 130 relative to the catheter shaft 120 and/or the guidewire 200. The motor 150 may be of any type suitable for the intended use, including but not limited to, pneumatic, electric, hydraulic, and/or combinations thereof. In at least some embodiments, the atherectomy apparatus 100 may include a suitable power source operably connected to the motor 150.

The drive housing 110 may include a longitudinal lumen 160 in fluid communication with the guidewire lumen 132 of the rotatable drive shaft 130. The longitudinal lumen 160 may be configured to receive the guidewire 200 such that the drive housing 110 is slidable over and/or may be configured to slide along the guidewire 200. For example, an inner diameter or inner extent of the longitudinal lumen 160 may be greater than an outer diameter or outer extent of the guidewire 200. In at least some embodiments, the longitudinal lumen 160 may extend through and/or may be accessible at a proximal portion and/or a proximal end of the drive housing 110. Some suitable but non-limiting materials for the atherectomy apparatus 100, the drive housing 110, the catheter shaft 120, the rotatable drive shaft 130, the rotatable cutting head 140, and/or the motor 150, for example metallic materials, polymer materials, composite materials, synthetic materials, etc., are described below.

Figure 2:
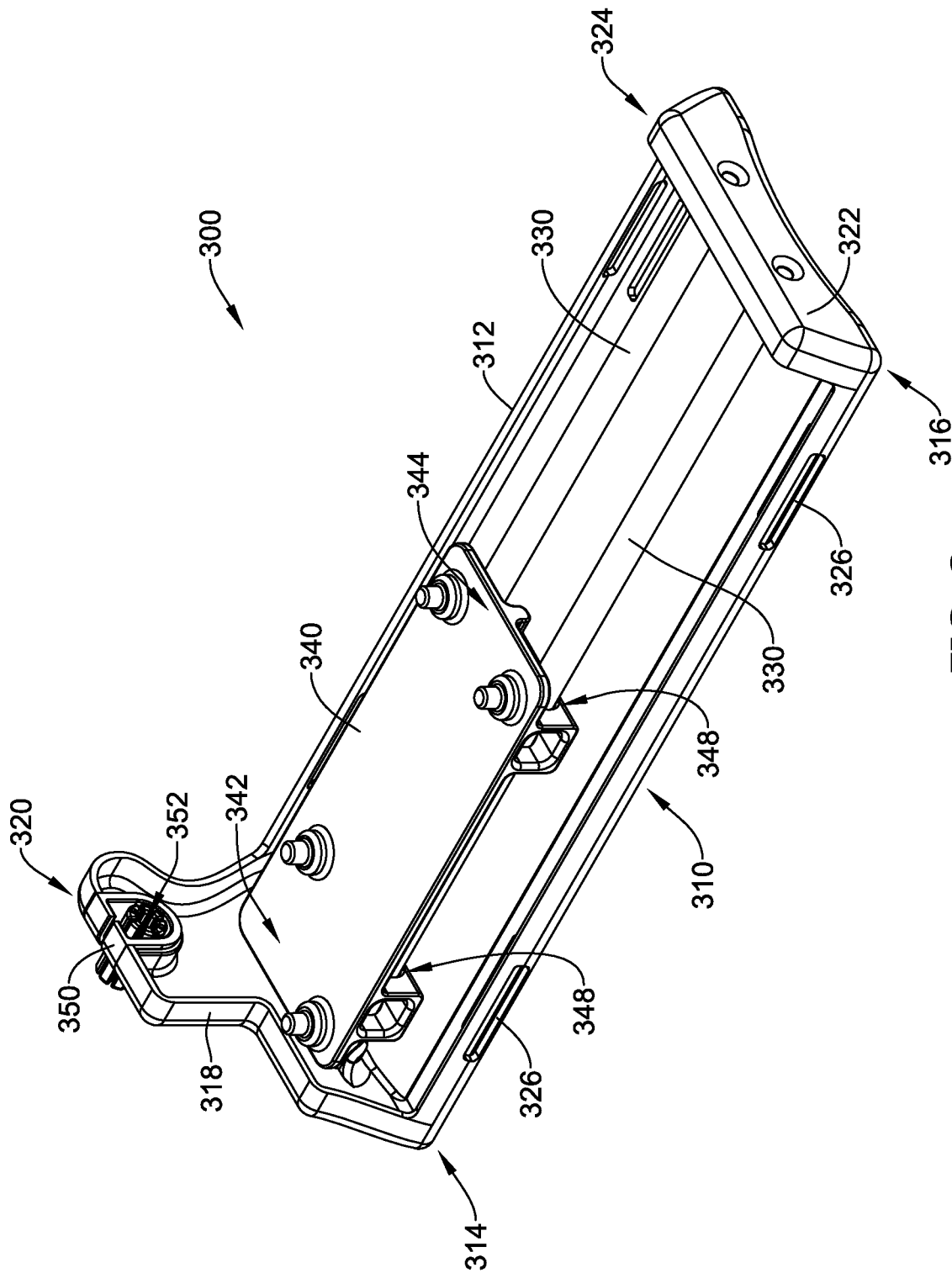
FIGS. 2 and 3 illustrate aspects of an example guidewire management device.
Figure 3:
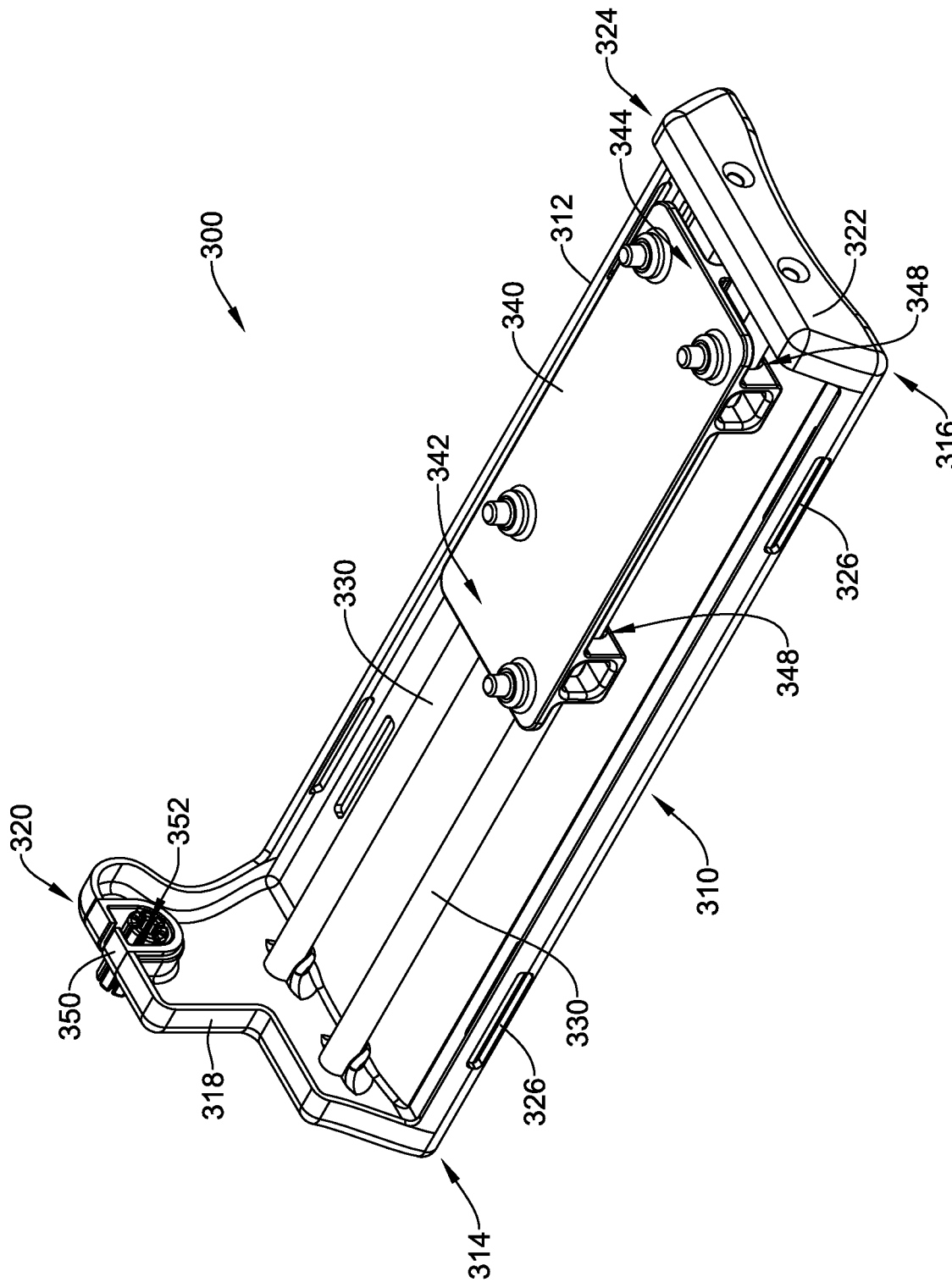

FIGS. 2 and 3 illustrate an example guidewire management device 300 comprising a frame 310 including at least one frame rail 330 extending longitudinally, a movable tray 340 slidably coupled to the at least one frame rail 330, and a guidewire locking element 350 secured and/or fixed to the frame 310. In some embodiments, the frame 310 may include a base 312 having a proximal end 314 and a distal end 316, a proximal upright 318, a distal upright 322, and the at least one frame rail 330 extending from the proximal upright 318 to the distal upright 322. The proximal upright 318 and the distal upright 322 may extend from a proximal end 314 and a distal end 316 of the base 312, respectively, at an oblique angle to the base 312. In some embodiments, the proximal upright 318 and the distal upright 322 may extend from the proximal end 314 and the distal end 316 of the base 312, respectively, substantially normal and/or perpendicular to the base 312. In some embodiments, a free end 320 of the proximal upright 318 may extend a greater distance from the base 312 than a free end 324 of the distal upright 322. In some embodiments, the proximal upright 318 and/or the distal upright 322 may be integrally formed with the base 312 as a single, unitary structure and/or from a single, monolithic piece of material.

In some embodiments, the frame 310 and/or the base 312 may include at least one slot 326 extending through the base 312. In some embodiments, the at least one slot 326 may comprise and/or include two slots, three slots, four slots, five slots, six slots, seven slots, eight slots, ten slots, or more, extending through a thickness of the base 312. In some embodiments, the at least one slot 326 may be used to affix the guidewire management device 300 and/or the frame 310 to a desired location, such as a table or a leg of the patient being treated. For example, a strap may be fed through the at least one slot 326 (or multiple straps may be fed through a plurality of slots) and used to secure the guidewire management device 300 and/or the frame 310 to the desired location. Other means of securement and/or uses for the at least one slot 326 are also contemplated.

In some embodiments, the at least one frame rail 330 may comprise and/or include two frame rails, three frame rails, four frame rails, or more, extending longitudinally along the base 312 of the frame 310. In some embodiments, the at least one frame rail 330 may be oriented substantially parallel to the base 312. In some embodiments, the at least one frame rail 330 may be fixedly attached to the frame 310, the proximal upright 318, and/or the distal upright 322. In some embodiments, the at least one frame rail 330 may be fixedly attached to the frame 310, the proximal upright 318, and/or the distal upright 322 using and/or by adhesive(s), welding (e.g., sonic, friction, etc.), melting or reflow, chemical bonding, or other suitable means. In some embodiments, the at least one frame rail 330 may be removably attached to the frame 310, the proximal upright 318, and/or the distal upright 322. In some embodiments, the at least one frame rail 330 may be removably attached to the frame 310, the proximal upright 318, and/or the distal upright 322 using and/or by mechanical fasteners, threading, friction or interference fit, or other suitable means. In some embodiments, the at least one frame rail 330 may be integrally formed with the frame 310, the proximal upright 318, and/or the distal upright 322 as a single, unitary structure and/or from a single, monolithic piece of material.

The at least one frame rail 330 may include and/or be formed with a profile or outer extent having one or more of a variety of regular and/or irregular cross-sectional shapes. For example, the at least one frame rail 330 may have a cross-sectional shape that is circular, triangular, square, rectangular, pentagonal, oval or elliptical, or other shapes. The movable tray 340 may include at least one coupling aperture 348 configured to receive the at least one frame rail 330, thereby slidably coupling the movable tray 340 to the at least one frame rail 330 and/or the frame 310. In some embodiments, the at least one coupling aperture 348 may comprise and/or include two coupling apertures, three coupling apertures, four coupling apertures, or more. In some embodiments, the at least one coupling aperture 348 may include one or more pairs of coupling apertures. Each pair of coupling apertures may include a proximal coupling aperture proximate a proximal end 342 of the movable tray 340 and a distal coupling aperture proximate a distal end 344 of the movable tray 340. In at least some embodiments, each pair of coupling apertures may be configured to receive one of the at least one frame rail 330. For example, each pair of coupling apertures may be configured and/or aligned to receive the same frame rail.

The movable tray 340 may be configured to slide between a proximal position adjacent the proximal end 314 and/or the proximal upright 318, shown in FIG. 2 for example, and a distal position adjacent the distal end 316 and/or the distal upright 322, shown in FIG. 3 for example. In some embodiments, the movable tray 340 may be freely slidable along the at least one frame rail 330. In some embodiments, the movable tray 340 may include a brake configured to maintain the movable tray 340 in a constant, user-selectable position along the at least one frame rail 330. In some embodiments, the movable tray 340 and the at least one frame rail 330 may have sufficient friction and/or interference between them to prevent the movable tray 340 from sliding on its own or due to gravity if the frame 310 is tilted, for example, but the friction and/or interference may be relatively easily overcome by the user to slide the movable tray 340 along the at least one frame rail 330 without excessive effort.

In some embodiments, the guidewire management device 300 may include the guidewire locking element 350 secured and/or fixed to the proximal upright 318 of the frame 310. In some embodiments, the guidewire locking element 350 may include an aperture 352 passing through the proximal upright 318 of the frame 310 in a longitudinal direction generally parallel to the base 312 of the frame 310. In some embodiments, the guidewire locking element 350 may include a longitudinally-oriented slot configured to permit the guidewire 200 to be passed into the guidewire locking element 350 in a lateral and/or radial direction, generally perpendicular to a longitudinal axis of the guidewire 200.

In some embodiments, the guidewire locking element 350 may be configured to slidably receive the guidewire 200. In some embodiments, the guidewire locking element 350 may be configured to engage with an outer surface of the guidewire 200 and/or to selectively secure the guidewire 200 in place relative to the frame 310. In some embodiments, the guidewire locking element 350 may be configured to longitudinally secure the guidewire 200 relative to the frame 310. In some embodiments, the guidewire locking element 350 may be configured to prevent longitudinal movement of the guidewire 200 relative to the frame 310. In some embodiments, the guidewire locking element 350 may be configured to rotationally secure the guidewire 200 relative to the frame 310. In some embodiments, the guidewire locking element 350 may be configured prevent rotational movement between the guidewire 200 and the frame 310. In some embodiments, selectively securing the guidewire 200 in place relative to the frame 310 may prevent both longitudinal and rotational movement of the guidewire 200 relative to the frame 310. In some embodiments, the guidewire locking element 350 may include a collet and/or a threaded member configured to engage and squeeze a plurality of flexible fingers into contact with the outer surface of the guidewire 200, thereby securing the guidewire 200 in place relative to the frame 310. Other configurations of a guidewire locking element, including but not limited to a wire torquer, a wedge-based system, an offset-based system, and/or a clamshell or clamping system, are also contemplated. Some suitable but non-limiting materials for the guidewire management device 300, the frame 310, the at least one frame rail 330, the movable tray 340, and/or the guidewire locking element 350, for example metallic materials, polymer materials, composite materials, synthetic materials, etc., are described below.

Figure 4:
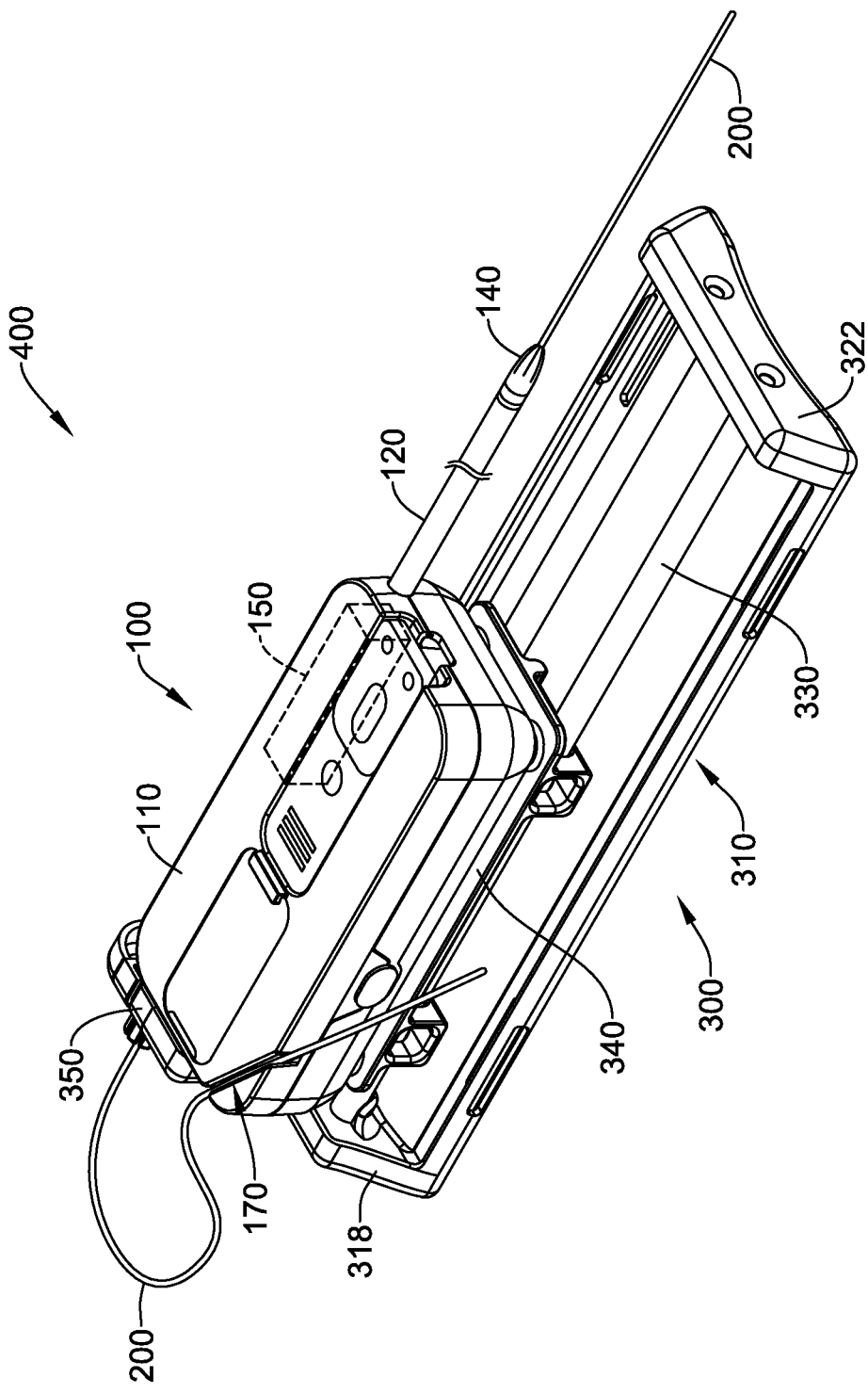
FIGS. 4 and 5 illustrate aspects of an example atherectomy system.
Figure 5:
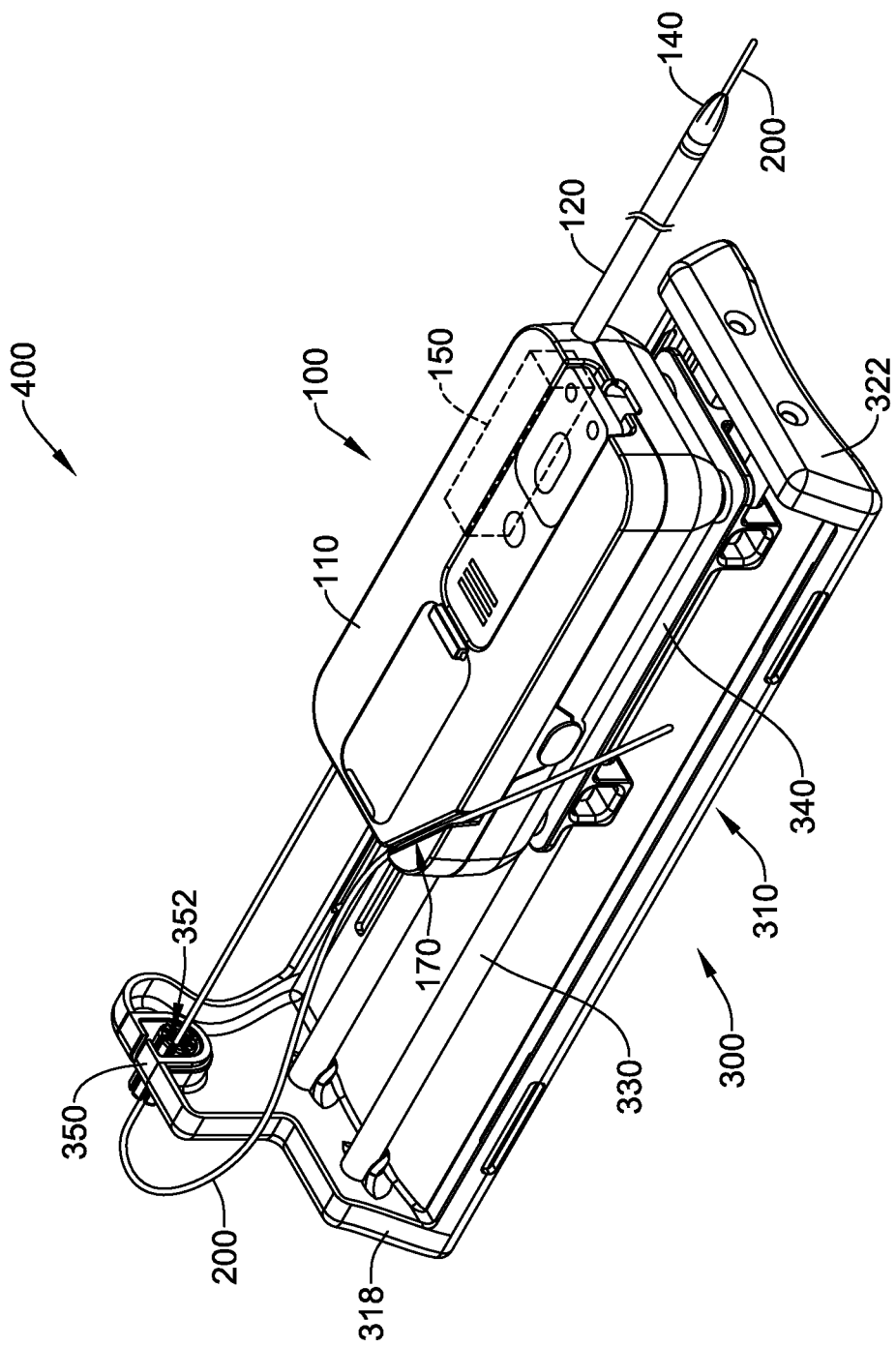

FIGS. 4 and 5 illustrate an example atherectomy system 400 comprising the atherectomy apparatus 100 and the guidewire management device 300. In some embodiments, the drive housing 110 of the atherectomy apparatus 100 may be configured to be releasably secured to the movable tray 340 of the guidewire management device 300 using any suitable means, including but not limited to mechanical fasteners, hook and loop fasteners, adhesive(s), snap fit, tab and slot connection(s), etc. In some embodiments, the movable tray 340 may include a plurality of mounting elements extending and/or projecting upward from the movable tray 340, the plurality of mounting elements being configured to engage with a corresponding plurality of receiving elements on and/or extending into the drive housing 110 of the atherectomy apparatus 100. In some embodiments, engagement of the plurality of mounting elements with the plurality of receiving elements may limit relative longitudinal movement between the movable tray 340 and the drive housing 110 of the atherectomy apparatus 100.

In use, the guidewire 200 may be advanced and/or navigated toward the target intervention site as described above. Next, the catheter shaft 120 of the atherectomy apparatus 100 may be advanced over the guidewire 200 toward the target intervention site. The drive housing 110 of the atherectomy apparatus 100 may be removably mounted and/or secured to the movable tray 340 of the guidewire management device 300 in the proximal position. In some embodiments, the drive housing 110 of the atherectomy apparatus 100 may be removably mounted and/or secured to the movable tray 340 of the guidewire management device 300 in the proximal position prior to advancing the catheter shaft 120 over the guidewire 200. In some embodiments, the drive housing 110 of the atherectomy apparatus 100 may be removably mounted and/or secured to the movable tray 340 of the guidewire management device 300 in the proximal position after advancing the catheter shaft 120 over the guidewire 200 to the target intervention site.

In some embodiments, the aperture 352 of the guidewire locking element 350 may be configured to receive the guidewire 200 fed therethrough. In some embodiments, the longitudinally-oriented slot of the guidewire locking element 350 may be configured to receive the guidewire 200 laterally and/or radially into the guidewire locking element 350. In some embodiments, the aperture 352 of the guidewire locking element 350 may be configured to receive the guidewire 200 fed therethrough prior to removably mounting and/or securing the drive housing 110 of the atherectomy apparatus 100 to the movable tray 340 of the guidewire management device 300. In some embodiments, the longitudinally-oriented slot of the guidewire locking element 350 may be configured to receive the guidewire 200 laterally and/or radially into the guidewire locking element 350 prior to removably mounting and/or securing the drive housing 110 of the atherectomy apparatus 100 to the movable tray 340 of the guidewire management device 300. In some embodiments, the aperture 352 of the guidewire locking element 350 may be configured to receive the guidewire 200 fed therethrough after removably mounting and/or securing the drive housing 110 of the atherectomy apparatus 100 to the movable tray 340 of the guidewire management device 300. In some embodiments, the longitudinally-oriented slot of the guidewire locking element 350 may be configured to receive the guidewire 200 laterally and/or radially into the guidewire locking element 350 after removably mounting and/or securing the drive housing 110 of the atherectomy apparatus 100 to the movable tray 340 of the guidewire management device 300.

When the positioning of the guidewire 200 and/or the catheter shaft 120 relative to the target intervention site is satisfactory, the guidewire locking element 350 may be engaged with and/or against the outer surface of the guidewire 200, thereby preventing longitudinal and/or rotational movement of the guidewire 200 relative to the frame 310. In some embodiments, the frame 310 may be secured in position relative to and/or at a desired location, using the at least one slot 326 for example, as described herein. Securing the frame 310 in position relative to and/or at the desired location may also fix the guidewire 200 in position relative to the target intervention site. In some embodiments, a distal end of the guidewire 200 may extend distally of the catheter shaft 120 and/or the rotatable cutting head 140 when the movable tray 340 is disposed in the proximal position.

The drive housing 110 and the movable tray 340 may be selectively and slidably advanced and/or retracted between the proximal position and the distal position, before, during, after, or any combination thereof, activating the motor 150 to cause rotation of the rotatable drive shaft 130 and/or the rotatable cutting head 140. While moving the drive housing 110 and the movable tray 340 relative to the frame 310, the guidewire 200 may remain fixed in position relative to the frame 310, and therefore the drive housing 110 and the catheter shaft 120 may be advanced and/or retracted over and/or relative to the guidewire 200, thereby avoiding and/or preventing unintentional longitudinal and/or rotational movement of the guidewire 200 relative to the target intervention site. In some embodiments, the distal end of the guidewire 200 may extend distally of the catheter shaft 120 and/or the rotatable cutting head 140 when the movable tray 340 is disposed in the distal position. The atherectomy system 400 may permit the advancement of the atherectomy apparatus 100 over the guidewire 200 by a single user while ensuring there are no inconsistencies between and/or unintended movements of the atherectomy apparatus 100 and the guidewire 200.

In some embodiments, the drive housing 110 may optionally include a guidewire brake slot 170 configured to receive the guidewire 200 and a guidewire brake configured to engage the guidewire 200 within the guidewire brake slot 170. In some embodiments, the guidewire brake may be configured to secure a proximal end of the guidewire 200 within the guidewire brake slot 170. The guidewire brake slot 170 may prevent the proximal end of the guidewire 200 from hanging loose below the atherectomy system 400 and/or the guidewire management device 300.

The materials that can be used for the various components of the atherectomy apparatus 100, the drive housing 110, the catheter shaft 120, the rotatable drive shaft 130, the rotatable cutting head 140, the guidewire 200, the guidewire management device 300, the frame 310, the at least one frame rail 330, the movable tray 340, and/or the guidewire locking element 350, etc. (and/or other systems or components disclosed herein) and the various elements thereof disclosed herein may include those commonly associated with medical devices. For simplicity purposes, the following discussion makes reference to the atherectomy apparatus 100, the drive housing 110, the catheter shaft 120, the rotatable drive shaft 130, the rotatable cutting head 140, the guidewire 200, the guidewire management device 300, the frame 310, the at least one frame rail 330, the movable tray 340, and/or the guidewire locking element 350, etc. However, this is not intended to limit the devices and methods described herein, as the discussion may be applied to other elements, members, components, or devices disclosed herein, such as, but not limited to, the motor 150, the base 312, the proximal upright 318, the distal upright 322, etc. and/or elements or components thereof.

In some embodiments, the atherectomy apparatus 100, the drive housing 110, the catheter shaft 120, the rotatable drive shaft 130, the rotatable cutting head 140, the guidewire 200, the guidewire management device 300, the frame 310, the at least one frame rail 330, the movable tray 340, and/or the guidewire locking element 350, etc., and/or components thereof may be made from a metal, metal alloy, polymer (some examples of which are disclosed below), a metal-polymer composite, ceramics, combinations thereof, and the like, or other suitable material. Some examples of suitable metals and metal alloys include stainless steel, such as 444V, 444L, and 314LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R44035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R44003 such as ELGILOY®, PHYNOX®, and the like); platinum enriched stainless steel; titanium; platinum; palladium; gold; combinations thereof; and the like; or any other suitable material.

As alluded to herein, within the family of commercially available nickel-titanium or nitinol alloys, is a category designated "linear elastic" or "non-super-elastic" which, although may be similar in chemistry to conventional shape memory and super elastic varieties, may exhibit distinct and useful mechanical properties. Linear elastic and/or non-super-elastic nitinol may be distinguished from super elastic nitinol in that the linear elastic and/or non-super-elastic nitinol does not display a substantial "superelastic plateau" or "flag region" in its stress/strain curve like super elastic nitinol does. Instead, in the linear elastic and/or non-super-elastic nitinol, as recoverable strain increases, the stress continues to increase in a substantially linear, or a somewhat, but not necessarily entirely linear relationship until plastic deformation begins or at least in a relationship that is more linear than the super elastic plateau and/or flag region that may be seen with super elastic nitinol. Thus, for the purposes of this disclosure linear elastic and/or non-super-elastic nitinol may also be termed "substantially" linear elastic and/or non-super-elastic nitinol.

In some cases, linear elastic and/or non-super-elastic nitinol may also be distinguishable from super elastic nitinol in that linear elastic and/or non-super-elastic nitinol may accept up to about 2-5% strain while remaining substantially elastic (e.g., before plastically deforming) whereas super elastic nitinol may accept up to about 8% strain before plastically deforming. Both of these materials can be distinguished from other linear elastic materials such as stainless steel (that can also be distinguished based on its composition), which may accept only about 0.2 to 0.44 percent strain before plastically deforming.

In some embodiments, the linear elastic and/or non-super-elastic nickel-titanium alloy is an alloy that does not show any martensite/austenite phase changes that are detectable by differential scanning calorimetry (DSC) and dynamic metal thermal analysis (DMTA) analysis over a large temperature range. For example, in some embodiments, there may be no martensite/austenite phase changes detectable by DSC and DMTA analysis in the range of about −60 degrees Celsius (° C.) to about 120° C. in the linear elastic and/or non-super-elastic nickel-titanium alloy. The mechanical bending properties of such material may therefore be generally inert to the effect of temperature over this very broad range of temperature. In some embodiments, the mechanical bending properties of the linear elastic and/or non-super-elastic nickel-titanium alloy at ambient or room temperature are substantially the same as the mechanical properties at body temperature, for example, in that they do not display a super-elastic plateau and/or flag region. In other words, across a broad temperature range, the linear elastic and/or non-super-elastic nickel-titanium alloy maintains its linear elastic and/or non-super-elastic characteristics and/or properties.

In some embodiments, the linear elastic and/or non-super-elastic nickel-titanium alloy may be in the range of about 50 to about 60 weight percent nickel, with the remainder being essentially titanium. In some embodiments, the composition is in the range of about 54 to about 57 weight percent nickel. One example of a suitable nickel-titanium alloy is FHP-NT alloy commercially available from Furukawa Techno Material Co. of Kanagawa, Japan. Other suitable materials may include ULTANIUM™ (available from Neo-Metrics) and GUM METAL™ (available from Toyota). In some other embodiments, a superelastic alloy, for example a superelastic nitinol can be used to achieve desired properties.

In at least some embodiments, portions or all of the atherectomy apparatus 100, the drive housing 110, the catheter shaft 120, the rotatable drive shaft 130, the rotatable cutting head 140, the guidewire 200, the guidewire management device 300, the frame 310, the at least one frame rail 330, the movable tray 340, and/or the guidewire locking element 350, etc., and/or components thereof, may also be doped with, made of, or otherwise include a radiopaque material. Radiopaque materials are understood to be materials capable of producing a relatively bright image on a fluoroscopy screen or another imaging technique during a medical procedure. This relatively bright image aids a user in determining the location of the atherectomy apparatus 100, the drive housing 110, the catheter shaft 120, the rotatable drive shaft 130, the rotatable cutting head 140, the guidewire 200, the guidewire management device 300, the frame 310, the at least one frame rail 330, the movable tray 340, and/or the guidewire locking element 350, etc. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of the atherectomy apparatus 100, the drive housing 110, the catheter shaft 120, the rotatable drive shaft 130, the rotatable cutting head 140, the guidewire 200, the guidewire management device 300, the frame 310, the at least one frame rail 330, the movable tray 340, and/or the guidewire locking element 350, etc. to achieve the same result.

In some embodiments, a degree of Magnetic Resonance Imaging (MRI) compatibility is imparted into the atherectomy apparatus 100, the drive housing 110, the catheter shaft 120, the rotatable drive shaft 130, the rotatable cutting head 140, the guidewire 200, the guidewire management device 300, the frame 310, the at least one frame rail 330, the movable tray 340, and/or the guidewire locking element 350, etc. For example, the atherectomy apparatus 100, the drive housing 110, the catheter shaft 120, the rotatable drive shaft 130, the rotatable cutting head 140, the guidewire 200, the guidewire management device 300, the frame 310, the at least one frame rail 330, the movable tray 340, and/or the guidewire locking element 350, etc., and/or components or portions thereof, may be made of a material that does not substantially distort the image and create substantial artifacts (e.g., gaps in the image). Certain ferromagnetic materials, for example, may not be suitable because they may create artifacts in an MRI image. The atherectomy apparatus 100, the drive housing 110, the catheter shaft 120, the rotatable drive shaft 130, the rotatable cutting head 140, the guidewire 200, the guidewire management device 300, the frame 310, the at least one frame rail 330, the movable tray 340, and/or the guidewire locking element 350, etc., or portions thereof, may also be made from a material that the MRI machine can image. Some materials that exhibit these characteristics include, for example, tungsten, cobalt-chromium-molybdenum alloys (e.g., UNS: R44003 such as ELGILOY®, PHYNOX®, and the like), nickel-cobalt-chromium-molybdenum alloys (e.g., UNS: R44035 such as MP35-N® and the like), nitinol, and the like, and others.

In some embodiments, the atherectomy apparatus 100, the drive housing 110, the catheter shaft 120, the rotatable drive shaft 130, the rotatable cutting head 140, the guidewire 200, the guidewire management device 300, the frame 310, the at least one frame rail 330, the movable tray 340, and/or the guidewire locking element 350, etc., and/or portions thereof, may be made from or include a polymer or other suitable material. Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, polyurethane silicone copolymers (for example, ElastEon® from Aortech Biomaterials or ChronoSil® from AdvanSource Biomaterials), biocompatible polymers, other suitable materials, or mixtures, combinations, copolymers thereof, polymer/metal composites, and the like. In some embodiments, the sheath can be blended with a liquid crystal polymer (LCP). For example, the mixture can contain up to about 6 percent LCP.

In some embodiments, the atherectomy apparatus 100, the drive housing 110, the catheter shaft 120, the rotatable drive shaft 130, the rotatable cutting head 140, the guidewire 200, the guidewire management device 300, the frame 310, the at least one frame rail 330, the movable tray 340, and/or the guidewire locking element 350, etc. may include and/or be formed from a textile material. Some examples of suitable textile materials may include synthetic yarns that may be flat, shaped, twisted, textured, pre-shrunk or un-shrunk. Synthetic biocompatible yarns suitable for use in the present invention include, but are not limited to, polyesters, including polyethylene terephthalate (PET) polyesters, polypropylenes, polyethylenes, polyurethanes, polyolefins, polyvinyls, polymethylacetates, polyamides, naphthalene dicarboxylene derivatives, natural silk, and polytetrafluoroethylenes. Moreover, at least one of the synthetic yarns may be a metallic yarn or a glass or ceramic yarn or fiber. Useful metallic yarns include those yarns made from or containing stainless steel, platinum, gold, titanium, tantalum or a Ni—Co—Cr-based alloy. The yarns may further include carbon, glass or ceramic fibers. Desirably, the yarns are made from thermoplastic materials including, but not limited to, polyesters, polypropylenes, polyethylenes, polyurethanes, polynaphthalenes, polytetrafluoroethylenes, and the like. The yarns may be of the multifilament, monofilament, or spun-types. The type and denier of the yarn chosen may be selected in a manner which forms a biocompatible and implantable prosthesis and, more particularly, a vascular structure having desirable properties.

In some embodiments, the catheter shaft 120, the rotatable drive shaft 130, the rotatable cutting head 140, the guidewire 200, etc. may include and/or be treated with a suitable therapeutic agent. Some examples of suitable therapeutic agents may include anti-thrombogenic agents (such as heparin, heparin derivatives, urokinase, and PPack (dextrophenylalanine proline arginine chloromethylketone)); anti-proliferative agents (such as enoxaparin, angiopeptin, monoclonal antibodies capable of blocking smooth muscle cell proliferation, hirudin, and acetylsalicylic acid); anti-inflammatory agents (such as dexamethasone, prednisolone, corticosterone, budesonide, estrogen, sulfasalazine, and mesalamine); antineoplastic/antiproliferative/anti-mitotic agents (such as paclitaxel, 5-fluorouracil, cisplatin, vinblastine, vincristine, epothilones, endostatin, angiostatin and thymidine kinase inhibitors); anesthetic agents (such as lidocaine, bupivacaine, and ropivacaine); anti-coagulants (such as D-Phe-Pro-Arg chloromethyl keton, an RGD peptide-containing compound, heparin, anti-thrombin compounds, platelet receptor antagonists, anti-thrombin antibodies, anti-platelet receptor antibodies, aspirin, prostaglandin inhibitors, platelet inhibitors, and tick antiplatelet peptides); vascular cell growth promoters (such as growth factor inhibitors, growth factor receptor antagonists, transcriptional activators, and translational promoters); vascular cell growth inhibitors (such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin); cholesterol-lowering agents; vasodilating agents; and agents which interfere with endogenous vasoactive mechanisms.

It should be understood that this disclosure is, in many respects, only illustrative. Changes may be made in details, particularly in matters of shape, size, and arrangement of steps without exceeding the scope of the invention. This may include, to the extent that it is appropriate, the use of any of the features of one example embodiment being used in other embodiments. The invention's scope is, of course, defined in the language in which the appended claims are expressed.

What is claimed is:

1. An atherectomy system, comprising:
   an atherectomy apparatus including a drive housing, a catheter shaft extending distally from the drive housing, and a rotatable drive shaft extending within the catheter shaft and operably coupled to the drive housing, the rotatable drive shaft having a guidewire lumen configured to receive a guidewire; and
   a guidewire management device comprising:
      a frame including a base, a proximal upright extending upward from an upper surface of the base at a proximal end of the base, a distal upright extending upward from the upper surface of the base at a distal end of the base, a first frame rail extending longitudinally along the base, and a second frame rail extending longitudinally along the base parallel to the first frame rail;
      wherein the proximal upright includes a tall portion and a short portion extending laterally from the tall portion;
      wherein the first frame rail is attached to the tall portion of the proximal upright and the second frame rail is attached to the short portion of the proximal upright;
      a movable tray slidably coupled to the first frame rail and the second frame rail; and
      a guidewire locking element fixed to the frame;
   wherein the drive housing is releasably secured to the movable tray.

2. The atherectomy system of claim 1, wherein the guidewire locking element is configured to slidably receive the guidewire.

3. The atherectomy system of claim 2, wherein the guidewire locking element is configured to selectively secure the guidewire in place relative to the frame.

4. The atherectomy system of claim 3, wherein selectively securing the guidewire in place relative to the frame prevents both longitudinal and rotational movement of the guidewire relative to the frame.

5. The atherectomy system of claim 1, wherein the catheter shaft is removably secured to the drive housing.

6. The atherectomy system of claim 5, wherein the catheter shaft is fixed in position relative to the drive housing.

7. The atherectomy system of claim 1, wherein the rotatable drive shaft is rotatable relative to the guidewire.

8. The atherectomy system of claim 1, wherein the drive housing includes a motor disposed within the drive housing, the motor being configured to rotate the rotatable drive shaft relative to the catheter shaft.

9. The atherectomy system of claim 1, wherein the drive housing includes a longitudinal lumen in communication with the guidewire lumen of the rotatable drive shaft, the longitudinal lumen being configured to receive the guidewire such that the drive housing is slidable over the guidewire.

10. An atherectomy system, comprising:
an atherectomy apparatus including a drive housing, a catheter shaft extending from a distal end of the drive housing, and a rotatable drive shaft extending within the catheter shaft and operably coupled to a motor within the drive housing, the rotatable drive shaft having a guidewire lumen configured to receive a guidewire; and
a guidewire management device comprising:
a frame including a base having an upper surface, a proximal upright extending upward from the upper surface of the base at a proximal end of the base, a distal upright extending upward from the upper surface of the base at a distal end of the base, and at least one frame rail extending longitudinally from the proximal upright to the distal upright, wherein the at least one frame rail is in direct contact with the proximal upright and the distal upright;
a movable tray slidably coupled to the at least one frame rail; and
a guidewire locking element fixed to the frame;
wherein the catheter shaft is removably secured to the drive housing and non-rotatable relative to the drive housing when secured to the drive housing;
wherein the guidewire locking element is configured to longitudinally secure the guidewire relative to the frame;
wherein the rotatable drive shaft is configured to rotate relative to the guidewire and the catheter shaft;
wherein the guidewire locking element defines a proximal portion of the guidewire and a distal portion of the guidewire such that the proximal portion of the guidewire extends proximally from the guidewire locking element and the distal portion of the guidewire extends distally from the guidewire locking element;
wherein the drive housing is configured to slide along the distal portion of the guidewire;
wherein the drive housing includes a longitudinal lumen in communication with the guidewire lumen of the rotatable drive shaft, the longitudinal lumen being configured to receive the distal portion of the guidewire such that the drive housing is slidable over the guidewire;
wherein the drive housing includes a slot configured to receive the proximal portion of the guidewire.

11. The atherectomy system of claim 10, wherein the atherectomy apparatus includes a rotatable cutting head fixed to a distal end of the rotatable drive shaft.

12. The atherectomy system of claim 10, wherein the guidewire locking element is configured to prevent relative rotational movement between the guidewire and the frame.

13. The atherectomy system of claim 10, wherein the drive housing is configured to be releasably secured to the movable tray.

14. The atherectomy system of claim 10, wherein the at least one frame rail includes two frame rails extending longitudinally along the base of the frame from the proximal upright to the distal upright, wherein the two frame rails are in direct contact with the proximal upright and the distal upright.

15. A guidewire management device, comprising:
a frame including a base member, a proximal upright member, a distal upright member, and at least one frame rail extending longitudinally from the proximal upright member to the distal upright member;
wherein the proximal upright member and the distal upright member extend upward from an upper surface of the base member at a proximal end and a distal end of the base member, respectively;
wherein the proximal upright member includes a tall portion and a short portion laterally offset from the tall portion;
a movable tray slidably coupled to the at least one frame rail; and
a guidewire locking element secured to the tall portion of the proximal upright member.

16. The guidewire management device of claim 15, wherein the at least one frame rail is oriented substantially parallel to the base member.

17. The guidewire management device of claim 15, wherein the guidewire locking element includes an aperture passing through the tall portion of the proximal upright member generally parallel to the base member.

18. The guidewire management device of claim 15, wherein the proximal upright member and the distal upright member extend from the proximal end and the distal end of the base member, respectively, at an oblique angle to the base member.

19. The guidewire management device of claim 18, wherein a free end of the proximal upright member extends a greater distance from the base member than a free end of the distal upright member.

20. The guidewire management device of claim 15, wherein the proximal upright member and the distal upright member are integrally formed with the base member.

* * * * *